United States Patent
Brace et al.

(10) Patent No.: US 7,244,254 B2
(45) Date of Patent: Jul. 17, 2007

(54) AIR-CORE MICROWAVE ABLATION ANTENNAS

(75) Inventors: Christopher L. Brace, Middleton, WI (US); Daniel Warren van der Weide, Madison, WI (US); Paul F. Laeseke, Madison, WI (US); Fred T. Lee, Jr., Madison, WI (US)

(73) Assignee: Microblate, Middleton, WI (US)

( * ) Notice: Subject to any disclaimer, the term of this patent is extended or adjusted under 35 U.S.C. 154(b) by 0 days.

(21) Appl. No.: 11/236,985

(22) Filed: Sep. 28, 2005

(65) Prior Publication Data

US 2006/0276780 A1 Dec. 7, 2006

Related U.S. Application Data

(63) Continuation-in-part of application No. 10/834,802, filed on Apr. 29, 2004, now Pat. No. 7,101,369.

(60) Provisional application No. 60/710,815, filed on Aug. 24, 2005, provisional application No. 60/710,276, filed on Aug. 22, 2005, provisional application No. 60/707,797, filed on Aug. 12, 2005, provisional application No. 60/702,393, filed on Jul. 25, 2005, provisional application No. 60/690,370, filed on Jun. 14, 2005, provisional application No. 60/684,065, filed on May 24, 2005, provisional application No. 60/679,722, filed on May 10, 2005.

(51) Int. Cl.
*A61B 18/18* (2006.01)

(52) U.S. Cl. .................. 606/33; 607/101; 607/154; 607/156

(58) Field of Classification Search .................. 606/33; 607/101–102, 154, 156
See application file for complete search history.

(56) References Cited

U.S. PATENT DOCUMENTS

| | | | | | |
|---|---|---|---|---|---|
| 4,057,064 A | * | 11/1977 | Morrison et al. | ............ | 606/49 |
| 4,074,718 A | * | 2/1978 | Morrison, Jr. | ............... | 606/45 |
| 4,375,220 A | * | 3/1983 | Matvias | ..................... | 607/102 |
| 4,446,874 A | * | 5/1984 | Vaguine | ..................... | 607/156 |
| 4,901,719 A | * | 2/1990 | Trenconsky et al. | .......... | 606/49 |
| 5,281,213 A | * | 1/1994 | Milder et al. | ................. | 606/15 |
| 5,281,217 A | * | 1/1994 | Edwards et al. | .............. | 606/41 |
| 5,431,649 A | * | 7/1995 | Mulier et al. | ................. | 606/41 |
| 5,620,479 A | * | 4/1997 | Diederich | ..................... | 601/3 |
| 5,737,384 A | * | 4/1998 | Fenn | .......................... | 378/65 |
| 5,810,804 A | * | 9/1998 | Gough et al. | ................. | 606/41 |
| 6,044,846 A | * | 4/2000 | Edwards | ..................... | 128/898 |
| 6,188,930 B1 | * | 2/2001 | Carson | ..................... | 607/101 |
| 6,398,781 B1 | * | 6/2002 | Goble et al. | ................. | 606/41 |

(Continued)

*Primary Examiner*—Michael Peffley
*Assistant Examiner*—Alex Toy
(74) *Attorney, Agent, or Firm*—Medlen & Carroll, LLP

(57) ABSTRACT

A method and device delivers microwave power to an antenna through a coaxial cable utilizing air or other gases as its dielectric core. The cable includes supports made of low-loss materials to keep the inner conductor centered in the cable, and defining spaces therebetween for the air or gas. Channels in the supports allow the air or gas to circulate in the cable. The gas may be chilled or cooled to provide an addition level of heat dissipation. The device enables delivery of large amounts of power to tissue without undue heating of the feed cable or peripheral tissues, and without increasing the diameter of the feeding cable or antenna, keeping the antenna safe for percutaneous use.

21 Claims, 2 Drawing Sheets

U.S. PATENT DOCUMENTS

| | | | |
|---|---|---|---|
| 6,506,189 B1* | 1/2003 | Rittman et al. | 606/41 |
| 6,514,249 B1* | 2/2003 | Maguire et al. | 606/41 |
| 6,740,107 B2* | 5/2004 | Loeb et al. | 607/89 |
| 6,866,663 B2* | 3/2005 | Edwards et al. | 606/41 |
| 2002/0022836 A1* | 2/2002 | Goble et al. | 606/34 |
| 2002/0133148 A1* | 9/2002 | Daniel et al. | 606/34 |
| 2003/0024538 A1* | 2/2003 | Edwards et al. | 128/898 |
| 2003/0088242 A1* | 5/2003 | Prakash et al. | 606/33 |
| 2003/0208200 A1* | 11/2003 | Palanker et al. | 606/45 |
| 2005/0015081 A1* | 1/2005 | Turovskiy et al. | 606/33 |

* cited by examiner

AIR-CORE MICROWAVE ABLATION ANTENNAS

CLAIM OF PRIORITY

This application is a Continuation-In-Part of U.S. Non-Provisional Patent Application entitled "Triaxial Antenna for Microwave Tissue Ablation" filed Apr. 29, 2004 and assigned U.S. application Ser. No. 10/834,802, now U.S. Pat. No. 7,101,369, the entire disclosure of which is hereby herein incorporated by reference.

This application further claims priority to U.S. Provisional Patent Applications entitled "Segmented Catheter for Tissue Ablation" filed May 10, 2005 and assigned U.S. Application Ser. No. 60/679,722; "Microwave Surgical Device" filed May 24, 2005 and assigned U.S. Application Ser. No. 60/684,065; "Microwave Tissue Resection Tool" filed Jun. 14, 2005 and assigned U.S. Application Ser. No. 60/690,370; "Cannula Cooling and Positioning Device" filed Jul. 25, 2005 and assigned U.S. Application Ser. No. 60/702,393; "Intralumenal Microwave Device" filed Aug. 12, 2005 and assigned U.S. Application Ser. No. 60/707,797; "Air-Core Microwave Ablation Antennas" filed Aug. 22, 2005 and assigned U.S. Application Ser. No. 60/710,276; and "Microwave Device for Vascular Ablation" filed Aug. 24, 2005 and assigned U.S. Application Ser. No. 60/710,815; the entire disclosures of each and all of these applications are hereby herein incorporated by reference.

CROSS-REFERENCE TO RELATED APPLICATIONS

This application is related to co-pending U.S. Non-Provisional Patent Application entitled "Triaxial Antenna for Microwave Tissue Ablation" filed Apr. 29, 2004 and assigned U.S. application Ser. No. 10/834,802; and to U.S. Provisional Patent Applications entitled "Segmented Catheter for Tissue Ablation" filed May 10, 2005 and assigned U.S. Application Ser. No. 60/679,722; "Microwave Surgical Device" filed May 24, 2005 and assigned U.S. Application Ser. No. 60/684,065; "Microwave Tissue Resection Tool" filed Jun. 24, 2005 and assigned U.S. Application Ser. No. 60/690,370; "Cannula Cooling and Positioning Device" filed Jul. 25, 2005 and assigned U.S. Application Ser. No. 60/702,393; "Intralumenal Microwave Device" filed Aug. 12, 2005 and assigned U.S. Application Ser. No. 60/707,797; "Air-Core Microwave Ablation Antennas" filed Aug. 22, 2005 and assigned U.S. Application Ser. No. 60/710,276; and "Microwave Device for Vascular Ablation" filed Aug. 24, 2005 and assigned U.S. Application Ser. No. 60/710,815; the entire disclosures of each and all of these applications are hereby herein incorporated by reference.

FIELD OF INVENTION

The present disclosure relates generally to the field of tissue resection, coagulation, and hemostasis, and delivery of microwave energy to tissue. Specifically, the present disclosure relates to a method and device for the delivery of microwave power to an antenna through a coaxial cable utilizing air or other gases as its dielectric core.

BACKGROUND

Use of energy to ablate, resect or otherwise cause necrosis in diseased tissue has proven beneficial both to human and to animal health. Microwave ablation and hyperthermia are well-established techniques to heat tumors to the point of necrosis. Larger zones of necrosis and shorter treatment times may be realized by applying larger powers to the antenna. Antennas used to deliver energy at microwave frequencies (300 MHz–300 GHz) to tissue typically require a coaxial cable to feed energy to the antenna. A coaxial antenna is an antenna created from a coaxial transmission line—an electromagnetic structure whereby an inner conductor wire, a dielectric core and outer conductor wire share a common axis. Current coaxial antenna designs use a polymer [e.g., polytetrafluoroethylene (PTFE)] as the dielectric core. Small cable and antenna diameters are required to ensure the procedure is minimally-invasive and safe.

Limitations of the above techniques center on the power rating and diameter of the coaxial cable used to feed the antenna, as well as microwave losses inside the coaxial cable dielectric core. An approximately exponential relationship between cable diameter and power rating exists; that is, as cable diameter decreases, the amount of power that cable may handle without failure decreases exponentially. Losses inside the coaxial cable dielectric core cause heat to be generated when large microwave powers are applied. This causes undue heating of the feeding cable, which causes unwanted necrosis of tissue near the feed cable and is undesirable for patient safety. Thus, the antenna input power is limited by the amount of power the feeding cable may handle without failure and by peripheral heating caused by the feed cable. This, in turn, limits the size of the zone of necrosis obtained in a given time. For this reason, current microwave ablation and hyperthermia antennas are limited in their ability to be operated at high powers and still be safe for percutaneous use.

Therefore, there is a need for a method and device for the delivery of microwave power to tissue which overcomes the above identified disadvantages and limitations of, and which represents an improvement over current coaxial antenna designs. The present disclosure fulfills this need.

SUMMARY

This present disclosure relates to a method and device for the delivery of microwave (e.g. approximately 300 MHz and higher frequencies) power to an antenna through a coaxial cable having air or other gases ($CO_2$, argon, helium, etc.) as the dielectric core. The device uses small mechanical supports made of low-loss materials (e.g., PTFE) to keep the inner conductor centered in the cable. The device enables delivery of large amounts of power to tissue without undue heating of the feed cable or peripheral tissues. This is accomplished without increasing the diameter of the feeding cable or antenna, which keeps the antenna safe for percutaneous use.

The supports and antenna may contain holes or channels to allow passage of circulating gases. The advantage of using gases for this purpose is that they have a low viscosity (to pass easily through the support and antenna channels), a very low conductivity, and the circulating gas can help cool the antenna. Circulation may be achieved from an external pump or compressor operatively connected with the cable. The gases may be chilled or cooled before entering the cable to provide an addition level of heat dissipation.

Accordingly, it is one of the objects of the present disclosure to provide a method and device for the delivery of microwave power to tissue.

It is a further object of the present invention to provide an improved co-axial cable for delivery of microwave energy to an antenna.

It is another object of the present invention to provide a coaxial cable utilizing air or other gases as its dielectric core.

Numerous other advantages and features of the disclosure will become readily apparent from the following detailed description, from the claims and from the accompanying drawings in which like numerals are employed to designate like parts throughout the same.

BRIEF DESCRIPTION OF THE DRAWINGS

A fuller understanding of the foregoing may be had by reference to the accompanying drawings wherein.

DESCRIPTION OF DISCLOSED EMBODIMENT(S)

Figure 1:
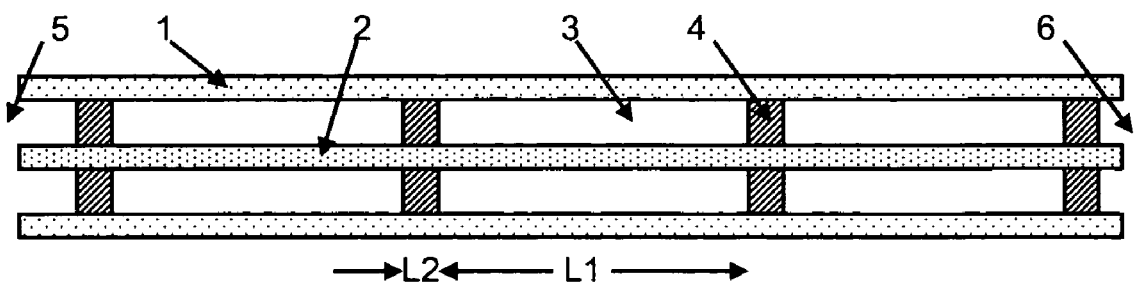
FIG. 1 is a longitudinal, cross-sectional view of the co-axial cable of the preferred embodiment of the present disclosure, showing the arrangement of the supports within the coaxial structure.

While the invention is susceptible of embodiment in many different forms, there is shown in the drawings and will be described herein in detail one or more embodiments of the present disclosure. It should be understood, however, that the present disclosure is to be considered an exemplification of the principles of the invention, and the embodiment(s) illustrated is/are not intended to limit the spirit and scope of the invention and/or the claims herein.

With reference to the drawings, the co-axial cable of the preferred embodiment of the present disclosure is shown. It should be understood that the cable can be of any suitable length, and the drawings figures are not intended to limit the length of the cable to the specific length illustrated or any specific length. Instead, it should be understood that only a representative portion or section of cable is illustrated.

FIG. 1 illustrates a semi-rigid coaxial cable, preferably constructed of copper or silver, utilizing air or other gas as the dielectric. The cable's inner conductor 2 is held with respect to the outer conductor 1 by supports 4 of length L2, separated by a distance L1. The length L2 is sufficiently short (~1 mm) to be much less than the wavelength inside the cable. L1 is as long as possible (~5–10 cm) to keep the inner conductor 2 centered with respect to the outer conductor 1. The gas dielectric 3 fills the space between each support. The cable can be chosen from commercially-available standards, but will be designed with a characteristic impedance of about 50 Ω.

It should be understood that the cable is connectorized or fixed to another feed cable on the proximal end 5, for connection with a power supply. It should also be understood that an antenna is connected or fixed to the distal end 6 of the cable in any suitable manner.

Figure 2:
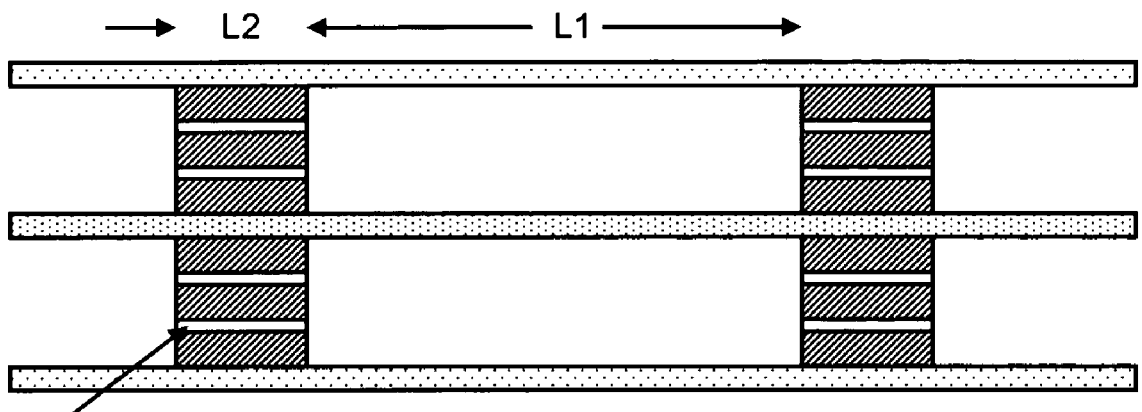
FIG. 2 is an enlarged longitudinal, cross-sectional view of a portion of the co-axial cable of the preferred embodiment of the present disclosure, and illustrating an alternate embodiment of the supports having channels therethrough.

Referring now to FIG. 2, an alternate embodiment of the supports 4 is illustrated. As can be seen, one or more channels 7 are provided in the supports 4, allowing for the air or gas 3 to flow between the spaces existing between each support 4. The number, pattern and size of the channels may be varied with gas flow requirements, gas viscosity or heating rate.

Figure 3:
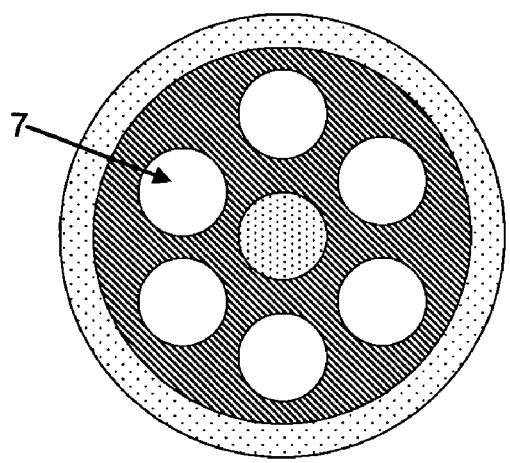
FIG. 3 is an enlarged axial, cross-sectional view the co-axial cable of the preferred embodiment of the present disclosure, and illustrating one embodiment of the arrangement of the channels in the supports.

FIG. 3 illustrates one example of the arrangement of channels 7 in the support 4. As can be seen in the embodiment illustrated in FIG. 3, six channels are generally equally spaced around the inner conductor 2, allowing for the circulation of air or other gas within the feed cable. As should be understood, an external pump or compressor can be operatively connected with the cable to circulate the air or gas. The air or gases may be chilled or cooled before entering the cable, or otherwise during circulation, to provide an addition level of heat dissipation.

Figure 4:
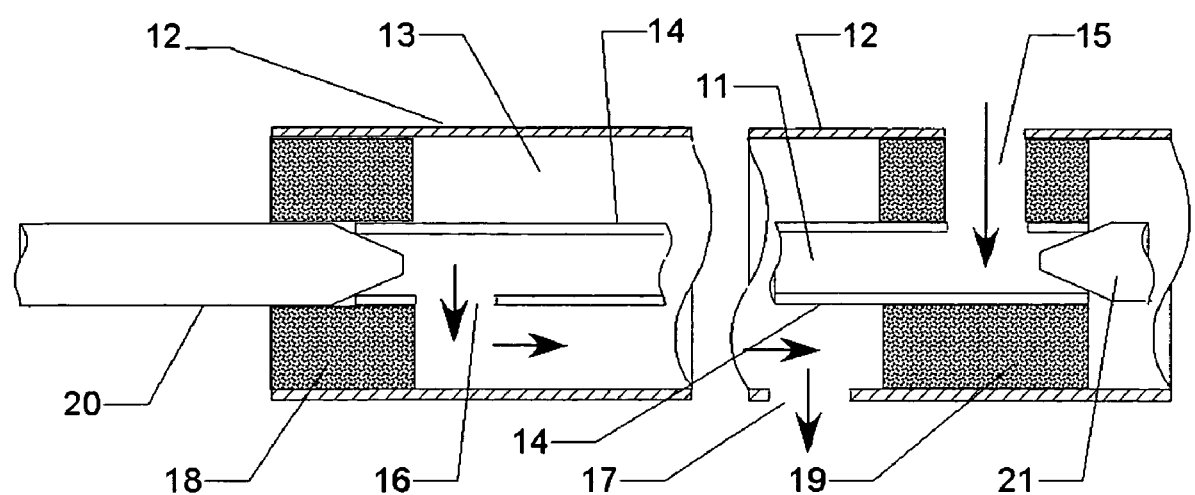
FIG. 4 is a longitudinal, cross-sectional view of an alternate embodiment of the present disclosure.

FIG. 4 is a longitudinal, cross-sectional view of another embodiment of the present disclosure, depicting a hollow center conductor with holes or channels for both introduction and exhaust of cooling gasses. The return flow of cooling gasses is through the interstitial space between center conductor and co-axial outer conductor. Also indicated are the distal and proximal joints between solid center conductors and the hollow center conductor.

As can be seen in FIG. 4, outer conductor 12 houses a dielectric core 13 for flow of air or other gasses, and further houses a center conductor 14, which is a hollow tube to conduct cooling gas along its length from one or more holes or channels at its proximal end 15 along its length to one or more holes or channels where the gas exits at its distal end 16. This exit 16 could also function as a venturi to allow for expansion of the gas as it changes pressure, further enhancing the cooling via the Joule-Thompson effect at the distal end of the co-axial cable. The gas is returned to the distal end through the core 13, and it exits through one or more holes or channels in the outer conductor 17. A non-conducting plug or support 18 at the distal end serves to support the center conductor, prevent the flow of cooling gas to the antenna at the distal end 20, and supports the joint between the antenna and the hollow-tube center conductor. A shaped and ported non-conducting plug or support 19 at the proximal end serves to introduce cooling gasses at 15, support the center conductor, prevent the flow of cooling gas to the solid center conductor at the proximal end 21, and support the joint between the solid center conductor and the hollow-tube center conductor.

It is to be understood that the embodiment(s) herein described is/are merely illustrative of the principles of the present invention. Various modifications may be made by those skilled in the art without departing from the spirit or scope of the claims which follow. For example, other applications of the co-axial cable disclosed herein are contemplated.

What is claimed is:

1. A device for delivery of microwave power to an antenna, comprising:

a coaxial cable having an outer conductor and an inner conductor; and a plurality of supports in the coaxial cable for holding and centering the inner conductor relative to the outer conductor, wherein a space is defined in the coaxial cable between adjacent supports; and a gas dielectric filling the space between adjacent supports such that the coaxial cable utilizes air or other gas as a dielectric core;

wherein the plurality of supports each have at least one flow channel allowing for the passage of gas through each support;

wherein the coaxial cable has a proximal end and a distal end, wherein the distal end is closed and the proximal end is open such that gas may only enter or exit the device through the proximal end of the coaxial cable.

2. The device of claim 1, wherein each support defines a length, and wherein the length of each support is sufficiently short to be much less than a wavelength inside the cable.

3. The device of claim 2, wherein the space between adjacent supports defines a distance, and wherein the distance of the space between adjacent supports is approximately 5 to 10 cm.

4. The device of claim 1, wherein each support defines a length, and wherein the length of each support is approximately 1 mm.

5. The device of claim 4, wherein the space between adjacent supports defines a distance, and wherein the distance of the space between adjacent supports is approximately 5 to 10 cm.

6. The device of claim 1, wherein the at least one flow channel comprises six channels generally equally spaced around the inner conductor.

7. The device of claim 1, further comprising a pump operatively connected with the coaxial cable, wherein the pump circulates the gas through the coaxial cable.

8. The device of claim 7 wherein the gas is chilled or cooled during circulation.

9. A device for combined delivery of microwave power to an antenna and cooling of the device comprising:
   a coaxial cable having an outer conductor and an inner conductor; and
   a plurality of supports in the coaxial cable for holding and centering the inner conductor relative to the outer conductor, wherein a space is defined in the coaxial cable between adjacent supports; and
   a gas dielectric filling the space between adjacent supports such that the coaxial cable utilizes air or other gas as a dielectric core;
   wherein at least a portion of the inner conductor comprises a hollow center allowing for the passage of gas through the hollow centers;
   wherein the coaxial cable has a proximal end and a distal end, wherein the distal end is closed and the proximal end is open such that gas may only enter or exit the device through the proximal end of the coaxial cable.

10. The device of claim 9, wherein the at least a portion of the inner conductor which comprises a hollow center further comprises at least one entrance port and at least one exit port for the gas.

11. The device of claim 10, wherein the at least a portion of the inner conductor which comprises a hollow center forms a joint at one end with a solid center portion of the inner conductor, and forms a joint at an opposite end with the antenna.

12. The device of claim 11, wherein a non-conducting plug supports the center conductor joints.

13. The device of claim 12, wherein the non-conducting plug supporting the joint at the end proximate the solid center portion includes a port in fluid communication with the least one entrance port, and wherein the outer conductor has a port proximate the at least a portion of the inner conductor which comprises a hollow center.

14. The device of claim 13, further comprising a pump operatively connected with the coaxial cable, wherein the pump circulates gas through the hollow center.

15. The device of claim 14, wherein the gas is chilled or cooled during circulation.

16. A device for combined delivery of microwave power to an antenna and cooling of the device comprising:
   a coaxial cable having an outer conductor and an inner conductor; and
   a plurality of supports in the coaxial cable for holding and centering the inner conductor relative to the outer conductor, wherein a space is defined in the coaxial cable between adjacent supports; and
   a gas dielectric filling the space between adjacent supports such that the coaxial cable utilizes air or other gas as a dielectric core;
   wherein at least a portion of the inner conductor comprises a hollow center allowing for the passage of gas through the hollow center and at least one entrance port and at least one exit port for the gas;
   wherein the at least a portion of the inner conductor which comprises a hollow center forms a joint at one end with a solid center portion of the inner conductor, and forms a joint at an opposite end with the antenna.

17. The device of claim 16, wherein a non-conducting plug supports the center conductor joints.

18. The device of claim 17, wherein the non-conducting plug supporting the joint at the end proximate the solid center portion includes a port in fluid communication with the least one entrance port, and wherein the outer conductor has a port proximate the at least a portion of the inner conductor which comprises a hollow center.

19. The device of claim 18, further comprising a pump operatively connected with the coaxial cable, wherein the pump circulates gas through the hollow center.

20. The device of claim 19, wherein the gas is chilled or cooled during circulation.

21. A method for delivery of microwave power to an antenna, comprising the steps of:
   defining spaces in a coaxial cable attached to the antenna, between an inner conductor and an outer conductor of the coaxial cable;
   holding and centering the inner conductor relative to the outer conductor with the plurality of supports each having at least one flow channel allowing for the passage of gas through each support circulating cooling gas between the spaces in the coaxial cable; and
   supplying power to the coaxial cable;
   wherein the coaxial cable has a proximal end and a distal end, wherein the distal end is closed and the proximal end is open such that gas may only enter or exit the device through the proximal end of the coaxial cable.

* * * * *